United States Patent [19]
Kawamura et al.

[11] Patent Number: 6,053,614
[45] Date of Patent: *Apr. 25, 2000

[54] OPHTHALMIC MEASURING APPARATUS WITH IMPROVED ALIGNMENT

[75] Inventors: Masunori Kawamura, Nagoya; Setsuo Saitou, Aichi, both of Japan

[73] Assignee: Nidek Company, Ltd., Japan

[*] Notice: This patent issued on a continued prosecution application filed under 37 CFR 1.53(d), and is subject to the twenty year patent term provisions of 35 U.S.C. 154(a)(2).

[21] Appl. No.: 08/595,822

[22] Filed: Feb. 2, 1996

[30] Foreign Application Priority Data

Feb. 2, 1995 [JP] Japan ..................................... 7-039279
Feb. 2, 1995 [JP] Japan ..................................... 7-039284

[51] Int. Cl.[7] ........................................................ A61B 3/10
[52] U.S. Cl. .......................... 351/211; 351/205; 351/208
[58] Field of Search .................................... 351/205, 208, 351/210, 211, 212, 221; 128/633, 745

[56] References Cited

U.S. PATENT DOCUMENTS 4,702,576 10/1987 Magnante .................................. 351/221
5,337,095 8/1994 Katsuragi et al. ....................... 351/208

*Primary Examiner*—Huy Mai
*Attorney, Agent, or Firm*—Rossi & Associates

[57] ABSTRACT

An ophthalmic measuring apparatus in one aspect of the invention for examining the crystalline lens of an eye having a measuring unit which projects a measuring light beam on the crystalline lens of the eye and receives the measuring light scattered by the crystalline lens comprises: a reference position setting means for setting a reference position for the eye in a three-dimensional space; a moving means for moving the measuring unit in a three-dimensional space relative to the eye; and a displacement detecting means for detecting the displacement of the measuring unit from the reference position for the eye. An ophthalmic measuring apparatus in another aspect of the invention, which irradiates the eyeball of an eye with a collimated beam of laser light and guides the laser light scattered by molecules of the crystalline lens of the eye through a light receiving optical system to a photoelectric transducer, comprises an observation optical system for observing the front of the eye, and a magnification changing means for changing the observation magnification of the observation optical system.

17 Claims, 6 Drawing Sheets

OPHTHALMIC MEASURING APPARATUS WITH IMPROVED ALIGNMENT

BACKGROUND OF THE INVENTION

1. Field of the Invention

The present invention relates to an ophthalmic measuring apparatus for examining the crystalline lens of the eye, and more particularly to improvements in the alignment system of an ophthalmic measuring apparatus for examining the crystalline lens by projecting a laser beam on the eyeball of the eye, guiding scattered laser light scattered by the crystalline lens through a light-receiving optical system to a photoelectric transducer and determining the condition of the crystalline lens on the basis of the output signals of the photoelectric transducer.

2. Description of the Related Art

A known ophthalmic measuring apparatus for examining the crystalline lens of the eye projects a laser beam on the crystalline lens, and detects scattered laser light scattered by molecules contained in the crystalline lens to examine the crystalline lens for cataract.

When aligning the ophthalmic measuring apparatus with a desired region on the crystalline lens, the examiner observes the crystalline lens and the laser beam through an observation optical system to determine the position of the ophthalmic measuring apparatus relative to the crystalline lens, and determines subjectively the position of the ophthalmic measuring apparatus relative to the desired region on the crystalline lens. The ophthalmic measuring apparatus makes a note of position data on the approximate relative position of the ophthalmic measuring apparatus on a memo sheet to store the position data for determining the position of the ophthalmic measuring apparatus relative to the same desired region in the next examination.

However, since the position data is determined subjectively by the examiner through the observation of the position of the laser beam relative to the crystalline lens of the eye, different position data are obtained by different examiners for the same desired region. Accordingly, the repeatability of the examination of the same desired region is low and, consequently, accurate age-based examination of the same desired region is impossible.

When aligning the ophthalmic measuring apparatus of this type with a measuring region, the positional relation between an image of the front of the eye and the laser beam is observed through the observation optical system. Therefore, a large magnification is used to achieve accurate alignment and minute observation of the measuring region and its vicinity.

However, when a large magnification is used, the rough observation of the eye is impossible and it is difficult to find the positional relation between the ophthalmic measuring apparatus and the eye. Consequently, the aligning operation takes a long time, exerting load on both the examiner and the subject.

SUMMARY OF THE INVENTION

The present invention has been made in view of the above circumstances and is intended to overcome the above mentioned problems.

Accordingly, it is an object of the present invention to provide an ophthalmic measuring apparatus capable of being quantitatively aligned with a desired measuring region and of being positioned relative to the measuring region in satisfactory repeatability for examination of the same measuring region after time has passed.

Another object of the present invention is to provide an ophthalmic measuring apparatus capable of being easily aligned with the eye and of facilitating the observation of the measuring region and its vicinity at a large magnification.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the invention, as embodied and broadly described herein, an ophthalmic measuring apparatus of this invention for examining the crystalline lens of an eye, comprises a displacement detecting means for detecting the displacement of a measuring unit, which projects a measuring light beam on the crystalline lens of the eye and receives the measuring light scattered by the crystalline lens, from a reference position for the eye; a scattered light intensity detecting means for detecting the intensity of the light scattered by the crystalline lens of the eye; an arithmetic means for calculating the protein composition of the crystalline lens of the eye on the basis of the intensity of the scattered light detected by the scattered light intensity detecting means; an information input means for entering information about the subject; a storage means for storing, in combination, information about the displacement of the measuring unit from the reference position for the eye detected by the displacement detecting means, information about the protein composition of the crystalline lens calculated by the arithmetic means, and information about the subject entered by operating the information input means; and a display means for displaying information about the displacement of the measuring unit from the reference position for the eye detected by the displacement detecting means.

The display means includes a means for displaying the displacement of the measuring unit from the reference position for the eye, detected by the displacement detecting means in the preceding examination.

The ophthalmic measuring apparatus further comprises an observation magnification changing means incorporated into an observation optical system for observing the anterior of the eye.

The observation magnification changing means is provided with a zoom lens disposed on the optical path of the observation optical system.

The observation magnification changing means is provided with a magnification changing lens which is selectively inserted in the optical path of the observation optical system.

According to the present invention it is capable of numerically specifying the position of the measuring region in the eye and hence the ophthalmic measuring apparatus can be accurately aligned with the measuring region.

Further, the ophthalmic measuring apparatus is capable of measuring the same measuring region in a high repeatability for measuring variations with time in the eye and of providing accurate measured results.

Since the magnification of the observation optical system can be varied according to the purpose of observation, a small magnification can be used for aligning the ophthalmic measuring apparatus with the measuring region and a large magnification can be used for easy observation of the measuring region and its vicinity. Accordingly, measurement can be quickly achieved and load on the examiner and the subject can be reduced.

BRIEF DESCRIPTION OF THE DRAWINGS

The accompanying drawings, which are incorporated in and constitute a part of this specification, illustrate embodiments of the invention and, together with the description, serve to explain the objects, advantages and principles of the invention. In the drawings.

DETAILED DESCRIPTION OF THE PREFERRED EMBODIMENTS

Preferred embodiments of the present invention will now be described hereinafter with reference to the accompanying drawings.

First Embodiment

[General Construction]

Figure 1:
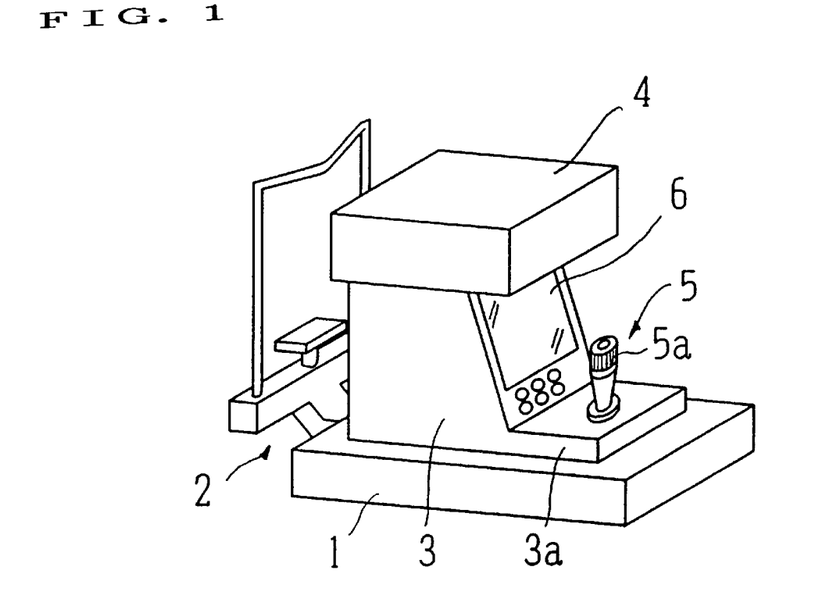
FIG. 1 is a general perspective view of an ophthalmic measuring apparatus in a first embodiment according to the present invention.
Figure 2:
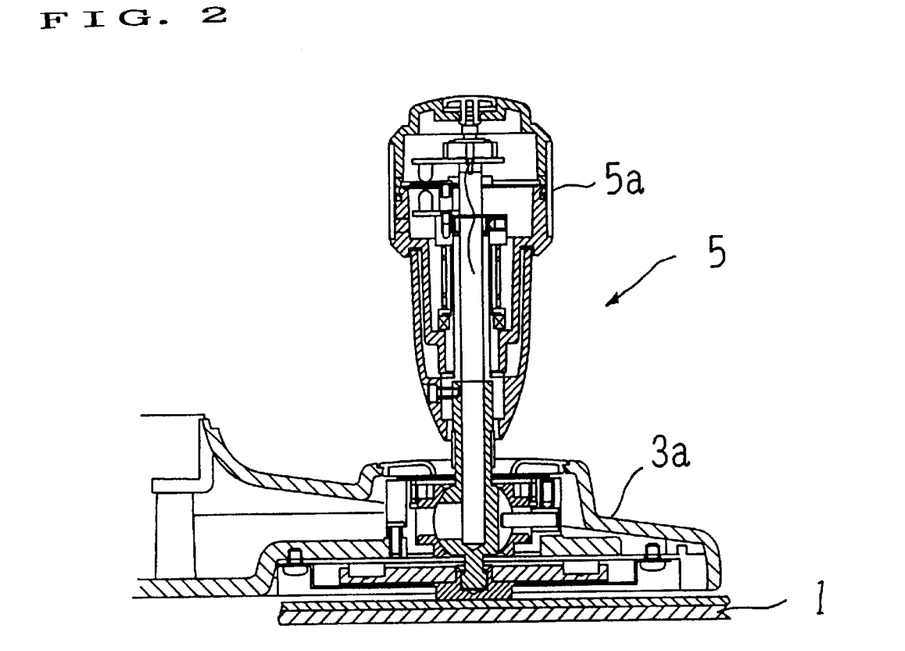
FIG. 2 is a sectional view of a joystick type moving mechanism included in the ophthalmic measuring apparatus of FIG. 1.

Referring to FIG. 1 showing an ophthalmic measuring apparatus in a first embodiment according to the present invention for examining the protein composition of the crystalline lens of an eye, there are shown a base 1, a head support 2 fixedly joined to the base 1 to support the head so that the position of the eye is fixed, a main unit 3, a measuring unit 4 containing optical systems, which will be described later, a joystick mechanism 5 for moving the main unit 3 and the measuring unit 4, and a monitor display 6 for displaying information for the examiner and the subject. The joystick of the joystick mechanism 5 is operated to move the main unit 3 longitudinally and laterally on the base 1 and to move the measuring unit 4 vertically relative to the main unit 3. The main unit 3 is moved minutely in horizontal directions relative to the base 1 by the cooperative actions of a spherical portion formed near the lower end of the joystick, the lower end of the joystick, a sliding plate moved by the lower end of the joystick, a friction plate attached to the base 1 so as to be in contact with the sliding plate, and a ball bearing held on the housing 3a of the main unit 3. The measuring unit 4 is moved vertically relative to the main unit 3 by the cooperative actions of a rotary knob 5a attached to the upper end of the joystick, a slit plate that turns together with the rotary knob 5a, a photodetector comprising a light source and a light receiving device disposed opposite to each other on the opposite sides of the slit plate, respectively, and fixedly held on the shaft of the joystick (FIG. 2), and a motor controlled on the basis of data on the direction and amount of rotation of the rotary knob 5a determined from the output signal of the light receiving device. Refer for the further details of the joystick mechanism 5 to "Joystick Mechanism for Ophthalmic Apparatus" disclosed in U.S. Pat. No. 5,406,076 granted to the applicant of the present patent application.

[System Constructions]

Optical System

Figure 3:
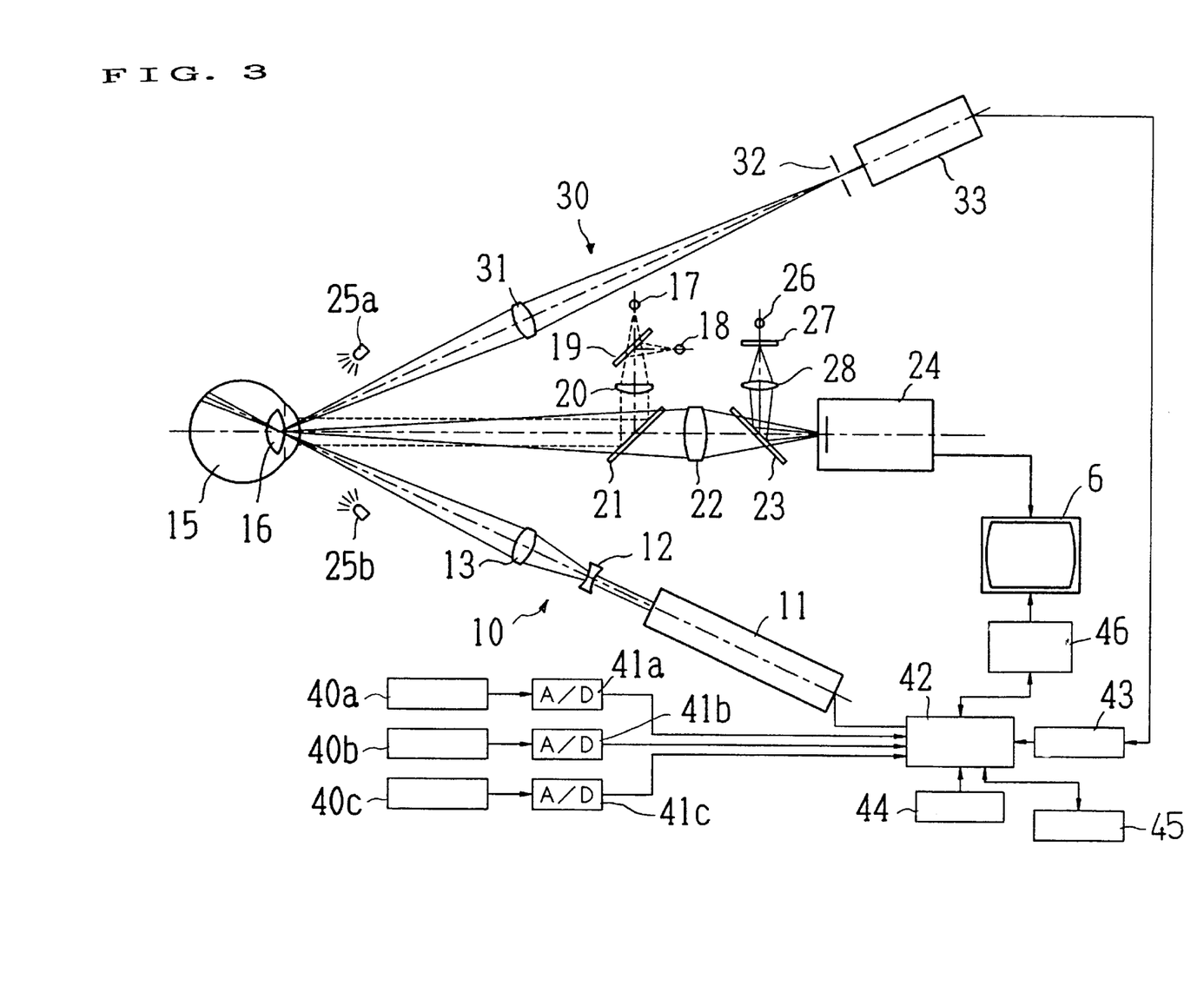
FIG. 3 is a block diagram, partly diagrammatic, of an optical system and an electrical system included in the ophthalmic measuring apparatus of FIG. 1.

Referring to FIG. 3, an optical system comprises a laser beam projecting optical system, a fixation/alignment optical system, an observation optical system, a reticle image projecting optical system and a scattered light receiving optical system.

(Laser Beam Projecting Optical System)

The laser beam projecting optical system 10 comprises a laser light source 11 that projects a laser beam of He—Ne visible laser light on the crystalline lens 16 of an eye 15, an expander lens 12, and a condenser lens 13 for gathering the laser beam on a measuring region on the crystalline lens 16.

(Fixation/Alignment Optical System)

The fixation/alignment optical system comprises an alignment light source 17 which emits infrared light for alignment, a point light source 18 which emits a visible light beam for fixation, a dichroic mirror 19 which transmits infrared light and reflects visible light, a collimator lens 20, and a beam splitter 21.

Alignment light emitted by the alignment light source 17 travels through the dichroic mirror 19, and is collimated by the collimator lens 20 in a light beam, and then the light beam is reflected by the beam splitter 21 onto the eye 15. Fixation light emitted by the fixation light source 18 is reflected by the dichroic mirror 19, and then the fixation light is directed toward the fundus of the eye 15 by the collimator lens 20 and the beam splitter 21.

(Observation Optical System)

The observation optical system comprises an image forming lens 22, a beam splitter 23 for aligning the optical axis of the observation optical system with that of the reticle image projecting optical system, a television camera 24, illuminating light sources 25a and 25b which emit near infrared light for illuminating the anterior of the eye 15. The television camera 24 takes an image of the front of the eye 15, and the monitor display 6 displays the image of the anterior of the eye 15.

(Reticle Image Projecting Optical System)

The reticle image projecting optical system comprises a reticle image projecting light source 26, a reticle plate 27 provided with a circular reticle, not shown, having its center at a position on the reticle plate 27 corresponding to the optical axis of image projection, and a projection lens 28. When the reticle image projecting light source 26 is turned on to illuminate the reticle plate 27, an image of the reticle is formed by the beam splitter 23 and the projection lens 28 on the image pickup device of the television camera 24, and the image of the reticle is displayed on the monitor display 6.

(Scattered Light Receiving Optical System)

The scattered light receiving optical system 30 comprises an image forming lens 31, an aperture 32 for limiting measuring region light flux, and a photoelectric transducer 33.

Electrical System

Referring to FIG. 3, an electrical system comprises potentiometers 40a and 40b for detecting the horizontal position of the main unit 3 relative to the base 1, a potentiometer 40c for detecting the vertical position of the measuring unit 4 relative to the main unit 3, A/D converters 41a, 41b and 41c for processing the output signals of the potentiometers 40a, 40b and 40c, respectively, a control circuit 42 which receives the output signals of the A/D converters 41a, 41b and 41c and controls the general operations of the ophthalmic measuring apparatus, an arithmetic circuit 43 which carries out operations for determining the auto correlation function of the intensity of the scattered light to examine the protein composition of the crystalline lens 16, an input unit 44 provided with switches for entering data including the ID number, the age and such of the subject, a reference position setting switch and command switches, a storage device 45, such as a storage circuit or a floppy disk, for storing measured data and the coordinates of the measuring region, and an image synthesizing circuit 46.

The control circuit 42 processes the signals by a well-known method to determine the horizontal and vertical displacements of the measuring unit 4 from a set reference position, which will be described later.

The potentiometers 40a, 40b and 40c, and the A/D converters 41a, 41b and 41c may be substituted with encoders and counters, respectively, or the relative positions of the main unit 3 and the measuring unit 4 may be detected by optical means.

The operations, principally, aligning operations, of the ophthalmic measuring apparatus thus constructed will be described.

The ophthalmic measuring apparatus is connected to a power source, the subject's head is positioned in place on the head support 2, and the subject is made to fix the eye 15 on the fixation light source 18. The examiner operates the joystick mechanism 5 for alignment. The image of the anterior of the eye 15 illuminated by the illuminating (light emitted by the illuminating) light sources 25a and 25b is received through the observation optical system together with the image of the reticle formed by the reticle image projecting optical system by the television camera 24, and the respective images of the anterior of the eye 15 and the reticle are displayed on the monitor display 6. The light emitted by the alignment light source 17 is collimated in an alignment light beam by the collimator lens 20, and the alignment light beam is reflected toward the eye 15 by the beam splitter 21. The alignment light beam forms a virtual image (alignment bright spot) at a position at a distance approximately equal to ½ the radius of curvature of the cornea of the eye 15. A light beam representing the alignment bright spot travels through the beam splitter 21 and the image forming lens 22 and falls on the image forming surface of the image pickup device of the television camera 24, and the image of the alignment bright spot is superposed on the respective images of the anterior of the eye 15 and the reticle on the screen of the monitor display 6. The examiner operates the joystick mechanism 5 while observing the images displayed on the monitor display 6 to move the measuring unit 4 relative to the eye 15 such that the image of the alignment bright spot coincides with the center of the image of the reticle and the image of the alignment bright spot is focused.

After the alignment bright spot has been positioned so as to meet a predetermined positional relation between the eye 15 and the alignment bright spot, the reference position setting switch of the input unit 44 is operated to enter data on a reference position for the eye 15 relative to the measuring unit 4 into the control circuit 42 and the arithmetic circuit 43.

After the reference position has been determined, the measuring unit 4 is aligned with the measuring region. The joystick mechanism 5 is operated to align the measuring unit 4 with a desired measuring region on the crystalline lens 16. When the main unit 3 and the measuring unit 4 are moved, the potentiometers 40a, 40b and 40c give signals corresponding to the positions of the main unit 3 and the measuring unit 4 to the control circuit 42. The control circuit 42 executes predetermined arithmetic operations on the basis of the input signals and determines coordinate data on the coordinates (x, y, z) of the measuring unit 4 relative to the reference position. The coordinate data is displayed numerically in a real-time mode on the monitor display 6 as shown in FIG. 4(a), in which indicated at 50 is the image of the alignment bright spot reflected by the cornea, at 51 is the image of the reticle, at 52 is is the laser beam passing the crystalline lens 16, and at 53 is the coordinate data.

After the measuring region has been thus determined, the key of a measurement switch provided on the joystick of the joystick mechanism 5 is depressed to start measurement. A laser beam of laser light emitted by the laser light source 11 is expanded by the expander lens 12 and then the expanded laser beam is gathered on the crystalline lens 16 of the eye 15 by the condenser lens 13. The laser beam is scattered by the crystalline particles in the measuring region and the scattered laser light is gathered by the image forming lens 31 of the scattered light receiving optical system 30 on the aperture 32, and the gathered scattered laser light travels through the aperture 32 and falls on the photoelectric transducer 33. The photoelectric transducer 33 gives an electric signal corresponding to the intensity of the scattered light to the arithmetic circuit 43. Then, the arithmetic circuit 43 executes predetermined arithmetic operations on the basis of the input signal, creates a correlation function representing the fluctuation of the intensity of the scattered laser light with time, and obtains measured data on the protein composition of the crystalline lens 16. The correlation function representing the variation of the intensity of the scattered light with time is expressed, for example, by the following expression mentioned in "Method of Detecting Cataract and Apparatus for Carrying out the Same" disclosed in International Publication No. WO 92/11799:

$$C(\tau)=\alpha(I_f \cdot e^{-\tau/\tau_f} + I_s \cdot e^{-\tau/\tau_s})^2 + (I_f + I_s + I_{imm})^2$$

where:

$\tau$ f: Constant relating to the size of not agglutinated particles
$\tau$ s: Constant relating to the size of agglutinated particles
If: Intensity of light scattered by not agglutinated particles
Is: Intensity of light scattered by agglutinated particles
Iimm: Intensity of light scattered by stationary particles
$\alpha$: Constant specific to the optical system.

The protein composition of the crystalline lens is calculated from the ratio (quantity) between the intensity If of light scattered by not agglutinated particles and the intensity Is of light scattered by agglutinated particles.

The measured data is given to the control circuit 42, the image synthesizing circuit 46 provides display data, the monitor display 6 displays an image represented by the measured data, and the storage device 45 stores the measured data. The coordinate data representing displacements of the measuring region from the reference position, and input data including the ID number and the age of the subject are stored in the storage device 45.

Figure 4:
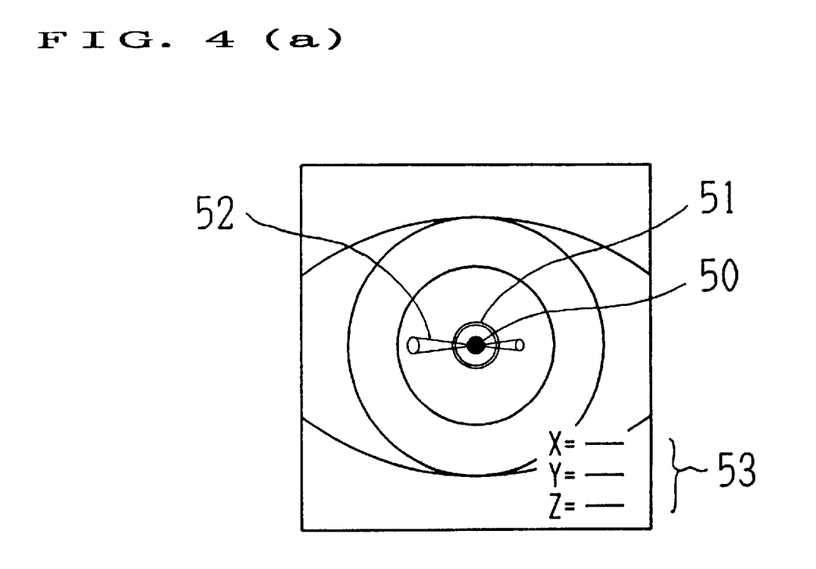
FIG. 4(a) is a pictorial view showing coordinate data displayed on the screen of a display.
FIG. 4(b) is a pictorial view showing coordinate data obtained in the preceding examination.

When measuring the same eye 15 again to examine the variation of the condition of the crystalline lens 16 with time, the ID number and the like are specified by operating the input unit 44, the coordinate data on the position of the measuring region determined in the preceding examination is retrieved from the storage device 45 and given through the image synthesizing circuit 46 to the monitor display 6 to display the coordinate data 54 obtained by the preceding examination as shown in FIG. 4(*b*).

In the succeeding examination, the same operations as those carried out in the preceding examination are carried out to focus the image of the alignment bright spot at the center of the image of the reticle, and the reference position setting switch is operated to redefine the reference position to reset the coordinate data 53 displayed on the screen of the monitor display 6 to the origin. The examiner operates the joystick mechanism 5 while observing the images displayed on the monitor display 6 to adjust the position of the measuring unit 4 so that the measuring unit 4 is aligned with the same measuring region examined in the preceding examination.

During the succeeding examination, directions in which the measuring unit 4 is to be moved, and distances for which the measuring unit 4 is to be moved may be determined on the basis of the displacement of the measuring unit 4 from the reference position determined in the preceding examination and the displacement of the same from the reference position determined in the succeeding examination, and arrows and the like indicating the directions and the distances may be displayed on the monitor display 6 to facilitate the aligning operation.

The reference position may be set automatically by image processing techniques. The position of the measuring unit 4 when the image of the alignment bright spot is formed at a predetermined position on the image pickup device of the television camera 24 in a predetermined size (or in a predetermined brightness) may be used as the reference position.

Second Embodiment

Figure 5:
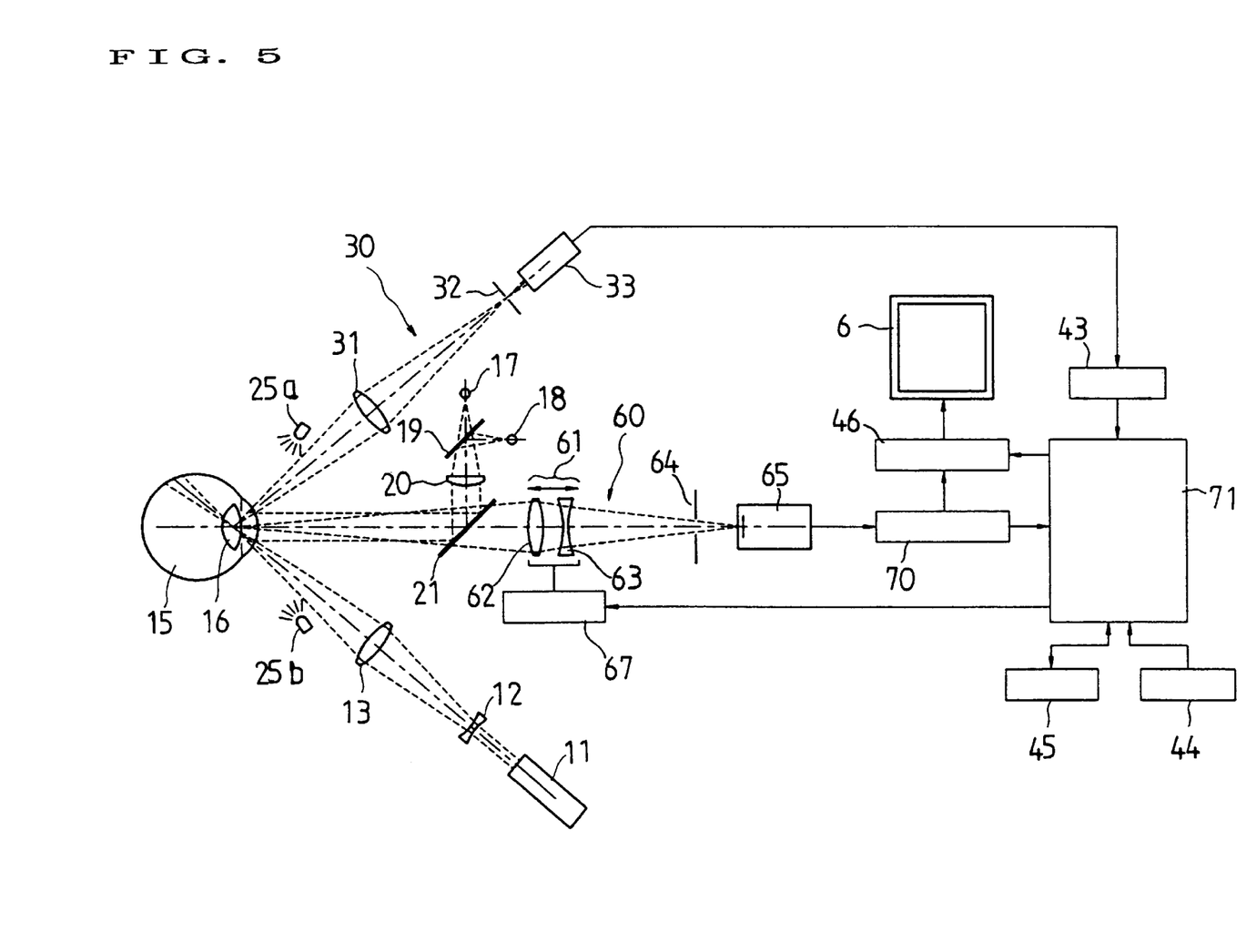
FIG. 5 is a block diagram, partly diagrammatic, of an ophthalmic measuring apparatus in a second embodiment according to the present invention.

FIG. 5 shows the optical system and the electrical system of an ophthalmic measuring apparatus in a second embodiment according to the present invention for measuring the protein composition of the crystalline lens of an eye. The optical system comprises a laser beam projecting optical system, a fixation/alignment optical system, an observation optical system and a scattered light receiving optical system.

Optical System

The laser beam projecting optical system 10, the fixation/alignment optical system (17 to 21) and the scattered light receiving optical system 30 (31 to 33) are the same as those of the ophthalmic measuring apparatus shown in FIG. 1; therefore, the components of those optical systems are designated by the same reference characters and the description thereof will be omitted.

(Observation Optical System)

The observation optical system 60 has a zoom lens 61 comprising an objective lens 62 and a concave lens 63. A zoom lens driving unit 67 moves the zoom lens 61 along the optical axis and changes the interval between the objective lens 62 and the concave lens 63 to vary the observation magnification. In FIG. 5, indicated at 64 is a diaphragm and at 65 is a CCD camera.

Electrical System

An image processing circuit 70 processes image signals provided by the CCD camera 65 by a predetermined method and gives the results of processing to a control computer 71. An image synthesizing circuit 46 combines characters and the like with an image formed by the CCD camera 65 and a monitor display 6 displays the output signals of the image synthesizing circuit 46. An arithmetic circuit 43 operates the output signals of a photoelectric transducer 33 to examine the protein composition of the crystalline lens. Functions of an input unit 44 and a storage device 45 are the same as those of the ophthalmic measuring apparatus shown in FIG. 1. The zoom lens driving unit 67 comprises a motor, a drive circuit and such.

The operation of the ophthalmic measuring apparatus will be described hereinafter. The subject's head is positioned in place on the head support 2, and the subject is made to fix the eye 15 on the fixation light source 18. The anterior of the eye 15 is illuminated by the illuminating light sources 25*a* and 25*b*, an image of the anterior of the eye 15 is formed on the imaging surface of the CCD camera 65 by the zoom lens 61 and the diaphragm 64. Image signals provided by the CCD camera 65 and representing the image of the anterior of the eye 15 are processed by the image processing circuit 70 and the image synthesizing circuit 46, and the image of the anterior of the eye 15 is displayed on the monitor display 6. During this operation, the zoom lens 61 is set for a small magnification to enable the examiner to observe the eye 15 entirely for rough alignment.

Figure 6:
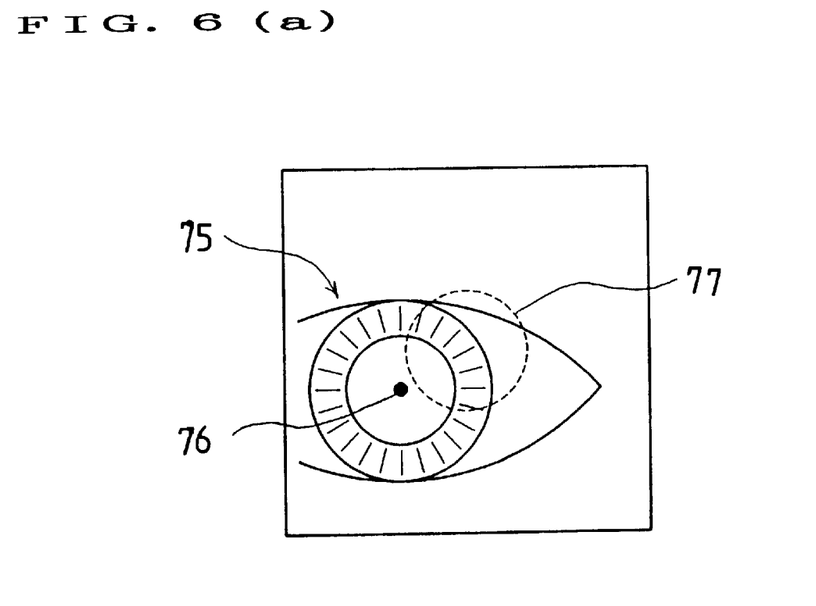
FIG. 6(a) is a pictorial view showing an image displayed on the screen of a display at a small magnification.
FIG. 6(b) is a pictorial view showing an image displayed on the screen of a display at a large magnification.

The light emitted by the alignment light source 17 travels through the dichroic mirror 19 and the collimator lens 20, and the alignment light beam is reflected toward the eye 15 by the beam splitter 21. The alignment light reflected by the surface of the cornea falls on the observation optical system. The alignment light travels through the zoom lens 61 and the diaphragm 64, and form a bright spot, i.e., an image of the alignment light reflected by the cornea, on the imaging surface of the CCD camera 65. FIG. 6(*a*) shows an image displayed on the monitor display 6 when the zoom lens 61 is set for a small magnification. In FIG. 6(*a*), indicated at 75 is an image of the anterior of the eye 15, at 76 is an alignment bright spot, and at 77 is an alignment mark produced by the image synthesizing circuit 46. The alignment mark may be formed by optical means. The examiner moves the optical system by operating the joystick, not shown, to move the alignment bright spot 76 into the alignment mark 77 while keeping the alignment bright spot 76 in the smallest possible size.

The image processing circuit 70 detects the position (and the size or the brightness) of the bright spot 76, and the control computer 71 decides whether or not the alignment bright spot 76 has been moved into the alignment mark 77 on the basis of the result of the detection. When it is decided that the bright spot 76 has been moved into the alignment mark 77, the control computer 71 actuates the zoom lens driving unit 67 to increase the magnification of the zoom lens 61 for observation at a large magnification. FIG. 6(*b*) shows an image displayed on the monitor display 6 when the zoom lens 61 is set for a large magnification.

A laser beam emitted by the laser light source 11 is expanded by the expander lens 12, is gathered by the condenser lens 13 and falls obliquely on the crystalline lens 16 of the eye 15. The image displayed at a large magnification as shown in FIG. 6(*b*) enables the minute observation of the crystalline lens 16 irradiated with the laser beam and hence the ophthalmic measuring apparatus can be accurately aligned with the measuring region.

After the measuring region has been decided, the measurement start switch of the input unit 44 is operated to start measurement. The laser light-projected on the crystalline lens 16 of the eye 15 is scattered in scattered light by protein particles in the crystalline lens 16. The scattered laser light travels through the image forming lens 31 and the aperture 32 for limiting the measuring region, and falls on the photoelectric transducer 33.

The photoelectric transducer 33 gives an electric signal corresponding to the intensity of the incident scattered laser light to the arithmetic circuit 43. The arithmetic circuit 43 creates a correlation function expressing the fluctuation of the intensity of the scattered laser light with time on the basis of the input signal. The control computer 71 determines the protein composition of the crystalline lens 16 by using the correlation function. The measured results are processed by the image synthesizing circuit 46, are displayed together with the image provided by the CCD camera 65 on the monitor display 6 and are stored in the storage device 45.

The observation magnification may be changed stepwise by controlling the zoom lens driving unit 67 so that the position of the zoom lens 61 is changed stepwise after the the eye 15 has been located.

Although this embodiment uses the alignment bright spot for deciding the aligned state, any other suitable means may be used for deciding the aligned state; for example, the position of the outline of the iris determined by processing the image may be used.

Third Embodiment

Figure 7:
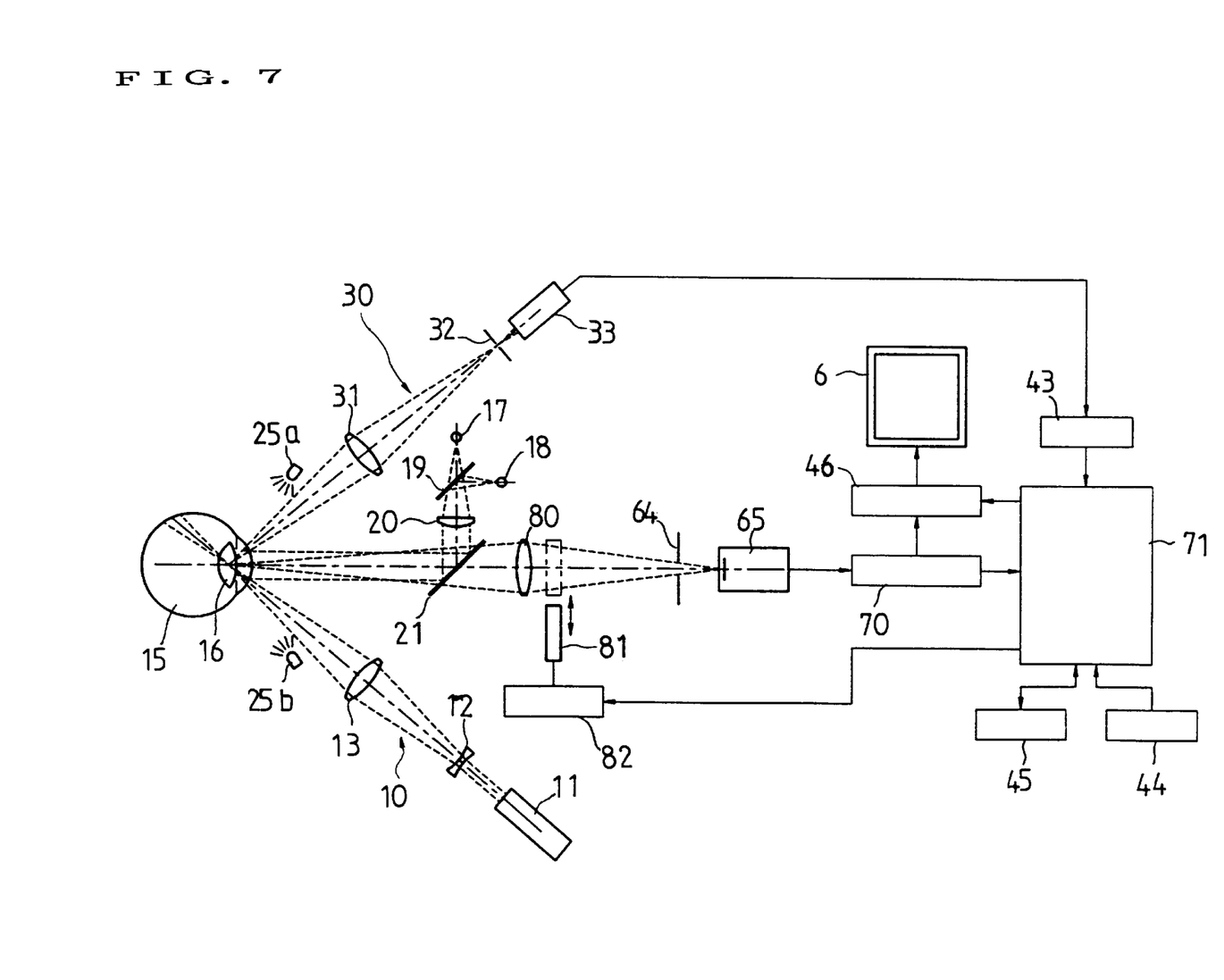
FIG. 7 is a block diagram, partly diagrammatic, of an ophthalmic measuring apparatus in a third embodiment according to the present invention.

FIG. 7 is a diagrammatic view of an ophthalmic measuring apparatus in a third embodiment according to the present invention.

The third embodiment employs, instead of the zoom lens 61, an image forming lens 80 and a magnification changing lens 81, and employs, instead of the zoom lens driving unit 67, a driving unit 82 for advancing the magnification changing lens 81 into and retracting the same from the observation optical path along which the observation light beam travels between the image forming lens 80 and a diaphragm 64. The observation optical system is set for the observation of the entire eye 15 at a small magnification by retracting the magnification changing lens 81 from the observation optical path or set for the observation of a local region of the eye 15 at a high magnification by advancing the magnification changing lens 81 into the observation optical path. A control computer 71 controls the driving unit 82 to advance the magnification changing lens 81 into or to retract the same from the observation optical path upon the detection of alignment of the ophthalmic measuring apparatus with the eye 15 by the image processing circuit 70.

When it is desired to change the magnification in a plurality of steps, the ophthalmic measuring apparatus is provided with a plurality of optical lenses 81 each having different magnification, and the control computer 71 controls the driving unit 82 to use those optical lenses sequentially upon the detection of alignment of the ophthalmic measuring apparatus with the eye 15.

In the foregoing embodiment, the ophthalmic measuring apparatus decides whether or not the measuring unit has been aligned with the eye on the basis of data obtained by processing an image provided by the CCD camera 65, and changes the observation magnification automatically. Naturally, the observation magnification may be changed by controlling the zoom lens 61 or the magnification changing lens 81 through the operation of switches and the like, while the examiner observes the image displayed on the monitor display 6. The zoom lens 61 and the magnification changing lens 81 may be operated by hand.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications are suited to the particular use contemplated. It is intended that the scope of the invention be defined by the claims appended hereto, and their equivalents.

What is claimed is:

1. An ophthalmic measuring apparatus for examining the crystalline lens of an eye, comprising:
    a measuring unit that projects a measuring light on the crystalline lens of the eye and receives the measuring light scattered by the crystalline lens from a reference position for the eye;
    a displacement detecting means for detecting the displacement of the measuring unit;
    a scattered light intensity detecting means for detecting the intensity of the measuring light scattered by the crystalline lens of the eye;
    an arithmetic means for calculating the protein composition of the crystalline lens of the eye on the basis of the intensity of the scattered measuring light detected by the scattered light intensity detecting means;
    an information input means for entering information about a subject;
    a storage means for storing, in combination, information about the displacement of the measuring unit from the reference position for the eye detected by the displacement detecting means, information about the protein composition of the crystalline lens calculated by the arithmetic means, and information about the subject entered by operating the information input means; and
    a display means for displaying information about the displacement of the measuring unit from the reference position for the eye detected by the displacement detecting means.

2. An ophthalmic measuring apparatus according to claim 1, wherein the display means includes a means for displaying the displacement of the measuring unit from the reference position for the eye, detected by the displacement detecting means in a preceding examination.

3. An ophthalmic measuring apparatus according to claim 1, further comprising an observation magnification changing means incorporated into an observation optical system for observing the anterior of the eye.

4. An ophthalmic measuring apparatus according to claim 3, wherein the observation magnification changing means is provided with a zoom lens disposed on the optical path of the observation optical system.

5. An ophthalmic measuring apparatus according to claim 3, wherein the observation magnification changing means is provided with a magnification changing lens that can be selectively inserted into and out of the optical path of the observation optical system.

6. An ophthalmic measuring apparatus for examining the crystalline lens of an eye comprising:
    a measuring unit that projects a measuring light on the crystalline lens of the eye and receives the measuring light scattered by the crystalline lens;
    a reference position setting means for setting a reference position defined in three-dimensional coordinates for a position of the eye;
    a moving means for moving the measuring unit in a three-dimensional space relative to the eye; and
    a displacement detecting means for detecting the displacement of the measuring unit moved by the moving means from the reference position.

7. An ophthalmic measuring apparatus according to claim 6, further comprising a display means for displaying the displacement detected by the displacement detecting means.

8. An ophthalmic measuring apparatus according to claim 6, further ccomprising a storage means for storing measured results corresponding to the measured light scattered by the crystalline lens and received by the measuring unit, and information about the displacement of a measuring unit detected by the displacement detecting means.

9. An ophthalmic measuring apparatus according to claim 8, further comprising a retreive means for reading information stored in the storage means.

10. An ophthalmic measuring apparatus according to claim 6, wherein the reference position setting means comprises: an observation optical system for observing the front of the eye; an alignment optical system which projects an alignment light beam on the cornea of the eye; and a position setting means for setting a reference position corresponding to the position of the measuring unit when a bright spot of the alignment light beam projected on and reflected by the cornea is located in a predetermined position relative to the eye.

11. An ophthalmic measuring apparatus according to claim 10, wherein the reference position setting means includes an input means to be operated by the examiner for entering information about the examination when the examiner decides that the bright spot is located in a predetermined position relative to the eye through observation by the observation optical system.

12. An ophthalmic measuring apparatus according to claim 11, wherein the displacement detecting means is provided with at least one of a potentiometer and an encoder.

13. An ophthalmic measuring apparatus according to claim 6, wherein the measuring unit comprises: a laser beam projecting optical system for irradiating the eyeball of an eye with a convergement beam of laser light; a scattered light receiving optical system for guiding the scattered laser light scattered by molecules contained in the crystalline lens to a photoelectric transducer; and an arithmetic means for calculating the protein composition of the crystalline lens on the basis of the output signals of the photoelectric transducer.

14. An ophthalmic measuring apparatus for examining the crystalline lens of an eye comprising:

means for irradiating an eyeball of an eye with a convergement beam of laser light;

a light receiving optical system for guiding scattered laser light scattered by molecules contained in a crystalline lens to a photoelectric transducer;

an observation optical system for observing the anterior of the eye;

a magnification changing means for changing the observation magnification of the observation optical system without changing a focal distance of the observation optical system, wherein the magnification changing means comprises an image pickup means for forming an image of the anterior of the eye, and a monitor display for displaying the image formed by the image pickup means;

an alignment means for performing a rough alignment, based on an image observed at low magnification with said observation optical system, and for performing a precise alignment, based on an image observed at high magnification with said observation optical system, by operation of said magnification changing means, wherein the alignment means includes an image processing means for processing the image formed by the image pickup means to generate processed image data, and a decision means for deciding whether or not the anterior of the eye is located at a predetermined observation position on the basis of the processed image data; and a light projecting means for projecting alignment light on the eye;

wherein the image processing means detects a position of an image of the alignment light projected by the light projecting means on the eye and reflected by the cornea of the eye.

15. An ophthalmic measuring apparatus according to claim 14, wherein the magnification changing means comprises a zoom lens disposed on the optical path of the observation optical system.

16. An ophthalmic measuring apparatus according to claim 14, wherein the magnification changing means comprises a magnfication changing lens that can be selectively inserted into and out of the optical path of the observation optical system.

17. An ophthalmic measuring apparatus according to claim 14, further comprising a control means for controlling the operation of a driving means for driving the magnification changing means on the basis of the decision made by the decision means.

* * * * *